US00PP21854P2

(12) United States Plant Patent
Burton

(10) Patent No.: US PP21,854 P2
(45) Date of Patent: Apr. 5, 2011

(54) ***AGAVE* PLANT NAMED 'AGAVWS'**

(50) Latin Name: *Agave attenuata*
Varietal Denomination: AGAVWS

(75) Inventor: Graeme John Burton, Ohaupo (NZ)

(73) Assignee: Lifetech Laboratories Ltd., Auckland (NZ)

( * ) Notice: Subject to any disclaimer, the term of this patent is extended or adjusted under 35 U.S.C. 154(b) by 0 days.

(21) Appl. No.: 12/592,120

(22) Filed: Nov. 19, 2009

(51) Int. Cl.
*A01H 5/00* (2006.01)

(52) U.S. Cl. ..... Plt./373

(58) Field of Classification Search ..... Plt./373, Plt./263.1
See application file for complete search history.

*Primary Examiner* — June Hwu
(74) *Attorney, Agent, or Firm* — Mark Bourgeois

(57) ABSTRACT

A new cultivar of *Agave* plant named 'AGAVWS' that is characterized by variegated leaves that are green with white margins.

1 Drawing Sheet

Botanical classification: *Agave attenuata.*
Variety denomination: 'AGAVWS'.

BACKGROUND OF THE INVENTION

The present invention relates to a new and distinct cultivar of *Agave* plant botanically known as *Agave attenuata* and hereinafter referred to by the cultivar name 'AGAVWS'.

'AGAVWS' is a naturally occurring whole plant mutation of *Agave* 'Tandarra's Tiger' (not patented). 'AGAVWS' was discovered in a greenhouse in a cultivated area of Hamilton, New Zealand in March of 2003.

Asexual reproduction first occurred by tissue culture in September of 2006 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Agave* cultivar 'AGAVWS'. These traits in combination distinguish 'AGAVWS' as a new and distinct cultivar apart from other existing known varieties of *Agave.*

1. *Agave* 'AGAVWS' exhibits variegated leaves that are green with white margins.

The closest comparison cultivar is the parent plant *Agave* 'Tandarra's Tiger'. The new cultivar 'AGAVWS' is distinguishable from 'Tandarra's Tiger' by the following characteristics:

1. 'AGAVWS' exhibits leaves that are green with white margins. The leaves of 'Tandarra's Tiger' are green with yellow margins.

'AGAVWS' can be compared to typical plants of the *Agave* species. The new cultivar 'AGAVWS' is distinguishable from typical plants of the *Agave* species by the following characteristics:

1. 'AGAVWS' exhibits leaves that are green with white margins. The leaves of typical plants of the *Agave* species are all green.

BRIEF DESCRIPTION OF THE DRAWING

The accompanying photograph illustrates the distinguishing traits of *Agave* 'AGAVWS'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Agave* cultivar named 'AGAVWS'. Data was collected in Hamilton, New Zealand from 2 year old outdoor grown plants. The time of year was Autumn in the Southern Hemisphere. The temperature range during the day was 10 to 25° Centigrade and 0-15° Centigrade at night. Color determinations are in accordance with The Royal Horticultural Society Colour Chart 2001 edition, except where general color terms of ordinary dictionary significance are used. The growing requirements are similar to the species. 'AGAVWS' has not been tested under all possible conditions and phenotypic differences may be observed with variations in environmental, climatic, and cultural conditions, however, without any variance in genotype.

Botanical classification: *Agave attenuata* 'AGAVWS'.
Annual or perennial: Perennial succulent.
Parentage: 'AGAVWS' is a naturally occurring whole plant mutation of *Agave* 'Tandarra's Tiger'.
Vigor: Moderate.
Growth habit: Clumping.
Height: 50 cm. in height.
Width: 80 cm. in width.
Low temperature tolerance: −2 degrees Centigrade.
High temperature tolerance: 30 degrees Centigrade.
Propagation: Tissue culture.
Time to produce a rooted cutting or liner (Summer): 3 months.
Time to produce a rooted cutting or liner (Winter): 5 months.
Crop time: 18 months to 24 months.
Root: Thick, fleshy.
Stem:
*Branching habit.*—Basal.
*Stem color.*—201A.
Foliage:
*Leaf arrangement.*—Rosette.
*Compound or single.*—Single.

*Quantity of leaves per plant.*—Average 28.
*Leaf shape.*—Elliptical.
*Leaf apex.*—Acute.
*Leaf base.*—Truncate.
*Leaf length.*—45 cm. in length.
*Leaf width.*—15 cm. in width.
*Texture.*—Both sides glabrous.
*Pubescence.*—Absent.
*Venation.*—Absent.
*Spines.*—Absent.
*Leaf margin.*—Entire.
*Young leaf color* (*lower surface*).—144D with margins 1 to 3 cm. wide white 155A.
*Young leaf color* (*upper surface*).—144C with margins 1 to 3 cm. wide white 155A.
*Mature leaf color* (*lower surface*).—147C with margins 1 to 3 cm. wide white 155A.
*Mature leaf color* (*upper surface*).—147B with margins 1 to 3 cm. wide white 155A.

Flowering: None observed.
Fruit/seed production: None Observed.
Disease and pest resistance: Resistance to diseases and pests has not been observed.

The invention claimed is:

1. A new and distinct variety of *Agave* plant named 'AGAVWS' as described and illustrated.

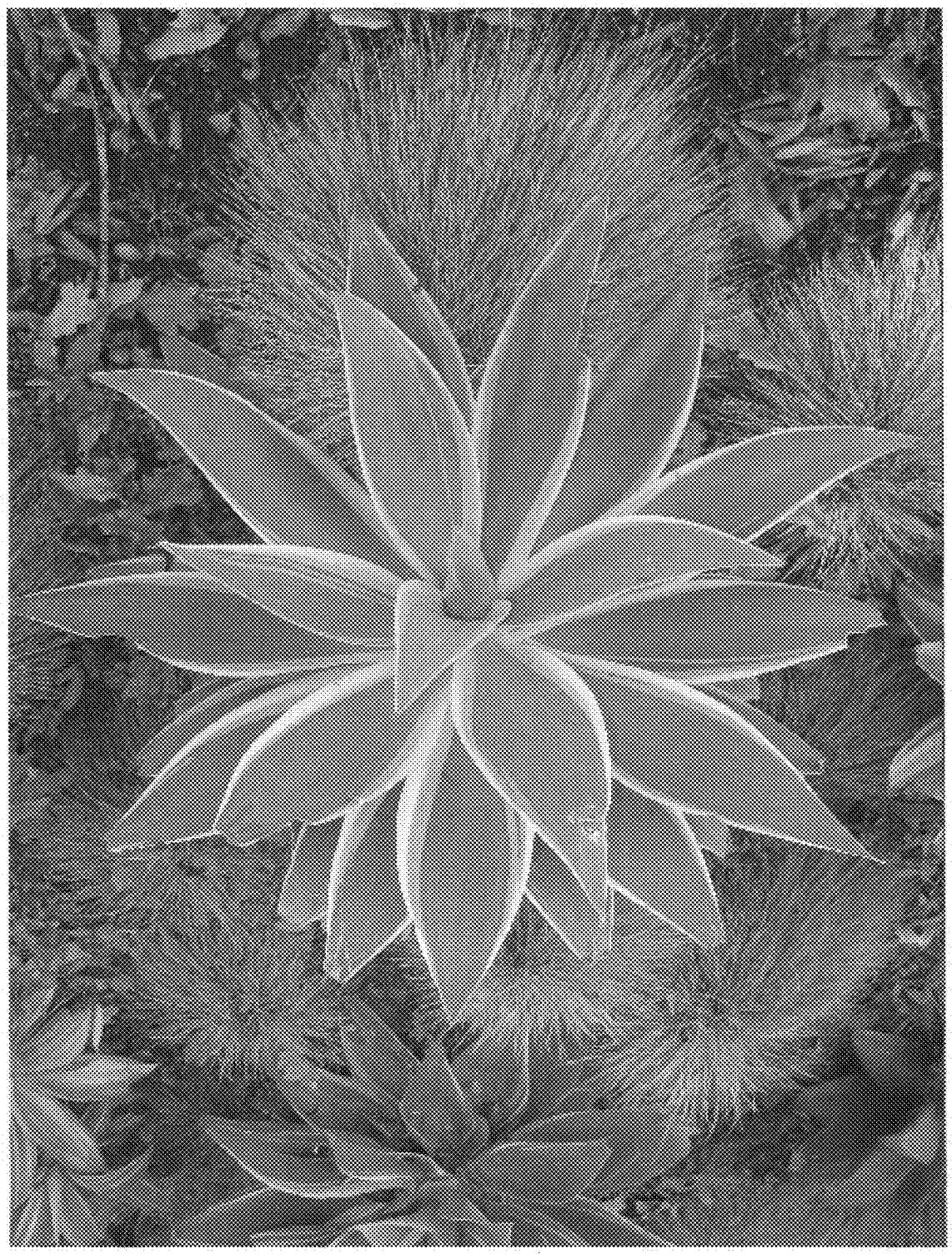

* * * * *